(12) United States Patent
Chung et al.

(10) Patent No.: US 10,961,208 B1
(45) Date of Patent: Mar. 30, 2021

(54) PRODUCT OF GLYCIDYL ETHER OF A MONO OR POLYHYDRIC PHENOL

(71) Applicant: CHANG CHUN PLASTICS CO., LTD., Taipei (TW)

(72) Inventors: Sung-Kuang Chung, Taipei (TW); An-Pang Tu, Taipei (TW)

(73) Assignee: CHANG CHUN PLASTICS CO., LTD., Taipei (TW)

(*) Notice: Subject to any disclaimer, the term of this patent is extended or adjusted under 35 U.S.C. 154(b) by 0 days.

(21) Appl. No.: 16/726,460

(22) Filed: Dec. 24, 2019

(51) Int. Cl.
| | |
|---|---|
| *C07D 301/28* | (2006.01) |
| *C08G 59/06* | (2006.01) |
| *C08L 63/00* | (2006.01) |
| *C08G 59/68* | (2006.01) |
| *C08K 5/17* | (2006.01) |

(52) U.S. Cl.
CPC ......... *C07D 301/28* (2013.01); *C08G 59/063* (2013.01); *C08G 59/686* (2013.01); *C08L 63/00* (2013.01); *C08K 5/17* (2013.01)

(58) Field of Classification Search
CPC ..... C08G 59/063; C08G 59/686; C08L 63/00; C07D 301/28; C08K 5/17
USPC .......................................................... 528/93
See application file for complete search history.

(56) References Cited

U.S. PATENT DOCUMENTS

| | | | |
|---|---|---|---|
| 2,943,096 A | 6/1960 | Reinking | |
| 4,284,573 A | 8/1981 | Arnett et al. | |
| 4,876,371 A | 10/1989 | Ito et al. | |
| 6,001,873 A | 12/1999 | Hwang et al. | |
| 6,984,716 B2 | 1/2006 | Hwang et al. | |
| 8,426,547 B2 | 4/2013 | Su et al. | |
| 10,138,325 B2 | 11/2018 | Chen et al. | |
| 2016/0017087 A1 | 1/2016 | Lal et al. | |
| 2018/0079915 A1* | 3/2018 | Peskens | C09D 5/185 |
| 2020/0087444 A1* | 3/2020 | Yamoto | C08K 5/0025 |

FOREIGN PATENT DOCUMENTS

| | | |
|---|---|---|
| CN | 108299165 A | 7/2018 |
| DE | 3635383 A1 | 4/1988 |
| EP | 0148817 A1 | 7/1985 |
| GB | 897744 A | 5/1962 |
| JP | H04353517 A | 12/1992 |

(Continued)

OTHER PUBLICATIONS

Hirota et al., WO 2018/225411 A1 machine translation in English used for citation, Dec. 13, 2018 (Year: 2018).*

(Continued)

*Primary Examiner* — David T Karst
(74) *Attorney, Agent, or Firm* — Polsinelli PC

(57) ABSTRACT

Products of glycidyl ether of a mono or polyhydric phenol as well as methods to manufacture the same. In some instances, the product of glycidyl ether of a mono or polyhydric phenol has an epoxy equivalent weight ("EEW") and a hydroxyl value ("HV"), wherein the epoxy equivalent weight multiplied by the hydroxyl value (EEW×HV) is a value from 1 to 10. A process for producing the product of glycidyl ether of a mono or polyhydric phenol typically includes reacting an epihalohydrin with a mono or polyhydric phenol in the presence of a catalyst to produce a halohydrin ether; and dehalogenating the halohydrin ether to form the product of glycidyl ether of a mono or polyhydric phenol.

19 Claims, 3 Drawing Sheets

(56) References Cited

FOREIGN PATENT DOCUMENTS

| | | | | |
|---|---|---|---|---|
| JP | 10316897 A | * | 12/1998 | ............... C09D 5/03 |
| JP | 2004262977 A | | 9/2004 | |
| JP | 2009051937 A | | 3/2009 | |
| JP | 2009073862 A | * | 4/2009 | ............. C08G 59/24 |
| JP | 2009084361 A | * | 4/2009 | ............. C08G 59/28 |
| JP | 2017155080 A | | 9/2017 | |
| WO | 2018225411 A1 | | 12/2018 | |

OTHER PUBLICATIONS

Koide et al., JP 10-316897 A machine translation in English used for citation, Dec. 2, 1998 (Year: 1998).*
Kobayashi et al., JP 2009-084361 A machine translation in English, Apr. 23, 2009 (Year: 2009).*
DIC Corporation, "EPICLON®", Mar. 2017 (Year: 2017).*
Kaji et al., JP 2009-073862 A machine translation in English, Apr. 9, 2009 (Year: 2009).*
B. Ellis, "Chemistry and Technology of Epoxy Resins", Springer Netherlands, Dordrecht, 1993.
"Epoxy Resin and Epoxy Coatings", Beijing, Chemical Industry Press, 2003.

* cited by examiner

PRODUCT OF GLYCIDYL ETHER OF A MONO OR POLYHYDRIC PHENOL

FIELD OF THE DISCLOSURE

The instant disclosure is directed to a product of glycidyl ether of a mono or polyhydric phenol as well as methods to manufacture the same. Additionally, the instant disclosure relates to applications of the product of glycidyl ether of a mono or polyhydric phenol.

BACKGROUND OF THE DISCLOSURE

Certain glycidyl ethers and methods for generically producing some glycidyl ethers have been described in textbooks, such as B. Ellis, *Chemistry and Technology of Epoxy Resins*, Springer Netherlands, Dordrecht, 1993 and *Epoxy Resin and Epoxy Coatings* (Beijing: Chemical Industry Press, 2003), both of which are incorporated herein in their entirety for all purposes.

Glycidyl ethers are traditionally produced by way of epoxidation reactions using peroxides or reactions of epihalohydrins with hydroxylic compounds to form glycidyl ether under basic conditions. Methods for producing glycidyl ethers from reactions of epihalohydrins with hydroxylic compounds can typically be grouped into two major categories. The first category is directed to polycondensation reactions where the hydroxyl groups react with the epihalohydrin under the basic conditions, thereby simultaneously carrying out ring-opening and ring-closing reactions. The second category is directed to processes that use a phase transfer catalyst to promote the reaction of the hydroxyl compound with the epihalohydrin to produce an intermediate, and then use a base to promote ring-closing reactions to form the glycidyl ether.

Methods that employ phase transfer catalysts are described in U.S. Pat. No. 2,943,096; UK Patent Publication No. GB 897744 A; U.S. Pat. No. 4,284,573; Japanese Patent Publication No. JP 04353517 A; and Chinese Patent Publication No. CN 108299165 A; which are all incorporated herein in their entireties for all purposes.

Certain types of glycidyl ethers may be desirable for electronics, such as those described in Japanese Patent Publication No. JP 60079031 A; Japanese Patent Publication No. JP 62030145 A; Japanese Patent Publication No. JP 62064817 A; German Patent Publication No.: DE 3635383 A1; and U.S. Pat. No. 4,876,371 A, which are all incorporated herein in their entireties for all purposes.

Japanese Patent Publication No. JP 2004262977, which is incorporated herein in its entirety for all purposes, attempts to improve the characteristics of glycidyl ether. However, Japanese Patent Publication No. JP 2004262977 greatly increases the epoxy equivalent and viscosity of the resin, causing difficulty in the application. Additional patent applications that disclose glycidyl ethers include Japanese Patent Publication No. JP 2009051937 A; Japanese Patent Publication No. JP 2017155080 A; and PCT Patent Publication No. WO 2018225411 A1, which are all incorporated herein in their entireties for all purposes.

There is a continuing need for improved glycidyl ethers compounds as many of the references disclosed above describe compounds and methods containing drawbacks.

SUMMARY OF THE DISCLOSURE

Aspects of the instant disclosure are directed to a product of glycidyl ether of a mono or polyhydric phenol as well as methods to manufacture the same. Additionally, the instant disclosure relates to applications of the product of glycidyl ether of a mono or polyhydric phenol.

Processes for producing glycidyl ether compounds do not typically produce a single compound, but produce a plurality of different compounds. The following structures are exemplary theoretical structures of the glycidyl ether compounds, wherein $R_1$, $R_2$, $R_3$ are independently selected from a mono or polyhydric phenol; $G_1$, $G_2$, $G_3$ are independently selected from none or glycidyl ether groups; n, p, q, and r are integers from 0 to 20:

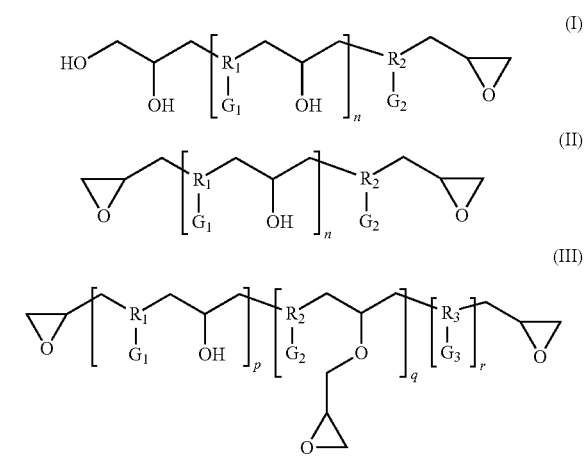

Structure (I), (II) and (III) represent alpha glycol compounds ("α-glycol"), normal glycidyl ether compounds and multiple glycidyl ether compounds ("MGE") respectively.

Due in part to the complexity of the numerous glycidyl ether compounds produced using traditional methods, it is conventionally believed to be difficult to simultaneously obtain glycidyl ether compounds having low hydrolyzable chlorine content, high dimensional stability, heat resistance, high temperature resistance required for high-electronic materials, low water absorption, and long pot life for composite materials.

The inventors discovered, however, that products of glycidyl ether of a mono or polyhydric phenol, as disclosed herein, may be obtained with many of the foregoing characteristics simultaneously improved by controlling the amount of epoxide functional groups and the amount of hydroxyl functional groups. For example, the products of glycidyl ether of phenol mono or polyhydric phenols desirably include a low amount of hydroxyl functional groups and a low amount of compounds containing a halogen group.

The product of glycidyl ether of a mono or polyhydric phenol typically comprise an epoxy equivalent weight ("EEW") and a hydroxyl value ("HV"), wherein the epoxy equivalent weight multiplied by the hydroxyl value (EEW× HV) is a value from 1 to 10. In some instances, the product of glycidyl ether of a mono or polyhydric phenol includes a value for EEW×HV of 1 to 9. The product of glycidyl ether of a mono or polyhydric phenol may have a value for EEW that is 150 to 200 g/eq and/or a value for HV that is from 0.01 to 0.06 eq/100 g. In at least one example, the product of glycidyl ether of a mono or polyhydric phenol may comprise 0.0001 to 0.11 mEq/g of alpha-glycol glyceryl ether groups. Additionally or alternatively, the product of glycidyl ether of a mono or polyhydric phenol may include 300 ppm or less of hydrolyzable chlorine.

The product of glycidyl ether of a mono or polyhydric phenol may be formed from a polyhydric phenol that is selected from resorcinol, hydroquinone, 2,2-bis-(4'-hydroxyphenyl)-propane (bisphenol A), mixtures of isomers of dihydroxydiphenyl methane (bisphenol F), 4,4'-di-hydroxydiphenyl cyclohexane, 4,4'-dihydroxy-3,3'-dimethyldiphenyl propane, 4,4'-dihydroxydiphenyl, 4,4'-dihydroxybenzophenone, bis-(4'-hydroxyphenyl)-1,1-ethane, bis-(4'-hydroxyphenyl)-1,1-isobutane, bis-(4'-hydroxy-tert.-butylphenyl)-2,2-propane, bis-(2-hydroxy-naphthyl)-methane,1,5-dihydroxynaphthalene, tris-(4-hydroxyphenyl)-methane, and bis-(4-hydroxy-phenyl) ether, bis-(4-hydroxyphenyl) sulfone, phenol novolak, brominated phenol novolak, o-cresol novolak, resorcin novolak, brominated resorcin novolak, tris(hydroxyphenyl)methane, tetraphenol ethane phenolic resin, aldehyde-polyphenolic condensates, dicyclopentadiene-phenolic resins, 9,10-dihydro-9-oxa-10-phosphaphenanthrene-10-oxide (DOPO) phenolic resins, and a combination thereof.

An epoxy resin composition may be obtained comprising a hardener and a product of glycidyl ether of a mono or polyhydric phenol, as discussed herein. Suitable hardeners for the expoxy resin composition may be selected from polyetheramine, isophoronediamine, 4,4-diaminodicyclohexylmethane, 4,4'-methylenebis(2-methylcyclohexylamine), 4-methyl-1,3'-cyclohexanediamine, dicyandiamide, imidazoles, phenol novolak, diaminodiphenylmethane, diaminodiphenylsulfone, m-phenylenediamine, phthalic anhydride, tetrahydrophthalic anhydride, pyrromellitic anhydride, benzophenone tetracarboxylic anhydride, and a combination thereof. In at least one instance, the hardener is isophoronediamine and the glass transition temperature of the epoxy resin composition after curing is more than 137° C. In at least one other instance, the hardener is isophoronediamine and the viscosity pot life of the epoxy resin composition after curing is from 40 to 100 minutes at a temperature of 30° C.

A process for producing the product of glycidyl ether of a mono or polyhydric phenol typically includes:
  (a) reacting an epihalohydrin with a mono or polyhydric phenol in the presence of a catalyst to produce a halohydrin ether; and
  (b) dehalogenating the halohydrin ether to form the product of glycidyl ether of a mono or polyhydric phenol.

The reaction of the epihalohydrin with a mono or polyhydric phenol may be carried out at a temperature of 30° C. to 80° C. In some instances, the process uses a molar ratio of the epihalodyrin to hydroxyl groups of the mono or polyhydric phenol, e.g., during the reaction step, that is from 3.5:1 to 11.0:1. Preferably, not more than 2 wt. % glycidol, based on the total weight of the epichlorohydrin, is present during the reaction of the epihalohydrin with the mono or polyhydric phenol. Additionally or alternatively, not more than 1 wt. % of water, based on the total weight of the epichlorohydrin, is present during the reaction of the epihalohydrin with the mono or polyhydric phenol.

The process for producing the product of glycidyl ether of a mono or polyhydric phenol may utilize a catalyst comprising an onium salt. In some cases, the onium salt is present in an amount of 1,000 to 9,000 ppm, relative to the total amount of mono or polyhydric phenol. Suitable onium salts include those selected from benzyltributylammonium chloride, benzyltriethylammonium chloride, benzyltrimethylammonium chloride, tetrabutylammonium bromide, tetramethylammonium chloride, tetrabutylammonium hydrogen sulfite, trioctylmethylammonium chloride and a combination thereof.

The halohydrin ether may be dehalogenated using a base. The base may be selected from an alkali metal or alkaline earth metal hydroxide, carbonate, bicarbonate, and a combination thereof. For example, the base may be selected from NaOH, KOH, $Na_2CO_3$, $K_2CO_3$, and a combination thereof.

BRIEF DESCRIPTION OF THE DRAWINGS

Implementation of the present technology will now be described, by way of example only, with reference to the attached figures, wherein.

Figure 1:
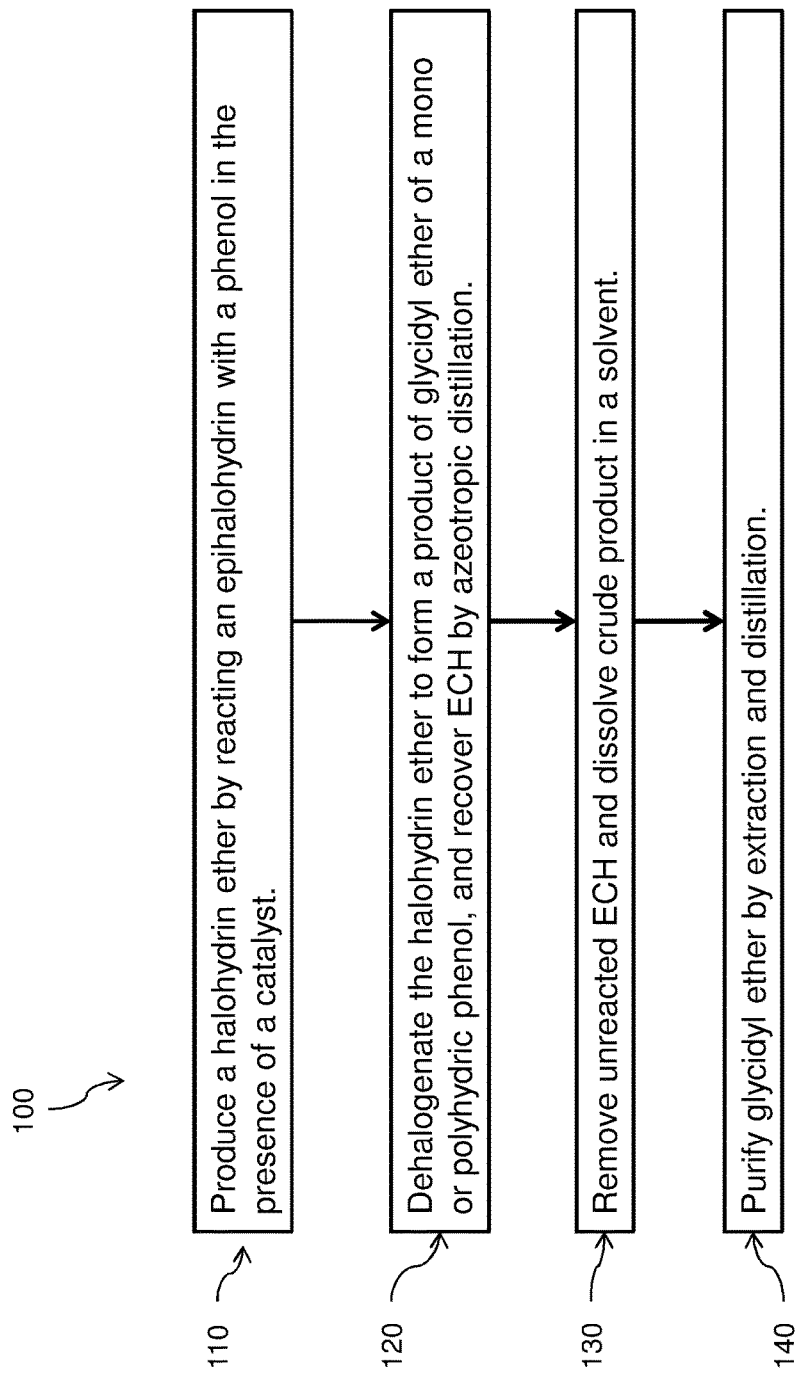
FIG. 1 is a flow chart depicting an exemplary method for producing a product of glycidyl ether of a mono or polyhydric phenol according to aspects of the disclosure.

It should be understood that the various aspects are not limited to the arrangements, instrumentality, and characteristics shown in the drawings.

DETAILED DESCRIPTION OF THE DISCLOSURE

Aspects of the instant disclosure are directed to a product of glycidyl ether of a mono or polyhydric phenol as well as methods to manufacture the same. Additionally, the instant disclosure relates to applications of the product of glycidyl ether of a mono or polyhydric phenol. As used herein, a product of glycidyl ether of phenol mono or polyhydric phenols is a composition comprising glycidyl ether compounds formed from mono or polyhydric phenol compounds. Polyhydric phenol compounds includes phenols having more than one hydroxyl group (e.g., dihydroxybenzenes), compounds containing more than one phenol (e.g., bisphenol A, polyphenols, etc.), and phenol resins (e.g., phenol formaldehyde resins).

In accordance with an aspect of the disclosure, methods are provided for producing polyglycidyl ethers of phenols. The methods of the instant disclosure may advantageously produce a product of glycidyl ethers of mono or polyhydric phenols having a high percentage of glycidyl ether groups relative to hydroxyl groups.

FIG. 1 depicts an exemplary method 100 for producing polyglycidyl ethers of phenols. As a brief overview, method 100 includes producing a halohydrin ether in step 110, dehalogenating the halohydrin ether and recovering epichlorohydrin ("ECH") by azeotropic distillation in step 120, removing unreacted ECH and dissolved crude product in a solvent in step 130, and purifying glycidyl ether by extraction and distillation in step 140.

In step 110, an ECH is reacted with a mono or polyhydric phenol in the presence of a catalyst to produce halohydrin ether. The reaction may be a coupling reaction that is carried out in the liquid phase, preferably with mixing. The temperature of the reaction mixture or solution may be from about 20° C. to about 200° C. For example, the reaction mixture or solution may be at a temperature of about 25° C.

to about 100° C., about 30° C. to about 80° C., about 35° C. to about 75° C., or about 40° C. to about 70° C., during the reaction.

The ECH employed in method 100 may be from a new ECH or recycled source, having less than less than 2 wt. % of glycidol and/or less than 1 wt. % water. For example, it may be desirable to utilize an ECH composition or source comprising at least 95 wt. % of ECH, preferably at least 97 wt. %, preferably at least 98 wt. %, preferably at least 99 wt. %, preferably at least 99.5 wt. % or preferably at least 99.9 wt. % of ECH. Additionally or alternatively, the halohydrin ether is preferably produced in a reaction mixture having not more than 2 wt. %, not more than 1.5 wt. %, not more than 1 wt. %, or not more than 0.5 wt. % of glycidol and/or not more than 1 wt. %, not more than 0.5 wt. %, not more than 0.3 wt. %, or not more than 0.1 wt. % of water, based on the total weigh of the ECH used for producing the halohydrin ether. While not intending to be limited to any specific thereof, the inventors believe that water and glycidol in the reaction may contribute to more hydrolysis compounds in the product (e.g., hydrolyzable chlorine, alpha glycol compounds, etc.) and result in high epoxy equivalent weight ("EEW") of the polyglycidyl ethers of phenols.

The amount of ECH and the amount of phenols may be controlled such that the molar ratio of the ECH to the phenolic hydroxy group ([ECH]/[OH]) is 3.5:1 to 11.0:1. In some instances, the molar ratio of the ECH to the phenolic hydroxy group(s) ([ECH]/[OH]) is from, 3.7:1 to 11.0:1, 4:1 to 10.74:1, 4:1 to 10:1, 4:1 to 9:1, 4:1 to 8:1, 4.5:1 to 10.74:1, 4.5:1 to 10:1, 4.5:1 to 9:1, or 4.5:1 to 8:1. Typically, the higher the value for ECH to the phenolic hydroxy group ([ECH]/[OH]) is, the more MGE compounds and the less OH groups in the product. For example, a greater value for [ECH]/[OH] may indicate more glycidyl ether groups and a lower EEW value. A greater value for [ECH]/[OH] may also indicate a lesser amount of hydroxyl groups and lower HV value. The inventors discovered that an increase in the value of [ECH]/[OH] may decrease or correlate to a decrease in the value of EEW×HV.

Preferably, the halohydrin ether is produced in the presence of a catalyst. The catalyst may be an onium salt, e.g., comprising at least one quaternary ammonium group and at least one halogen or phosphate group. For example, the catalyst could be a quaternary ammonium salt, quaternary phosphonium salt, crown ether, or a combination thereof. The catalyst may include or be formed from cations including tetramethylammonium, trimethyl-ethyl ammonium, dimethyl diethyl ammonium, triethylammonium, tripropylmethyl ammonium, tributyl-methyl ammonium, trioctylmethylammonium, tetraethylammonium, trimethyl-propyl ammonium, trimethyl phenyl ammonium, benzyltrimethylammonium, benzyltriethylammonium, diallyldimethylammonium, n-octyl trimethyl ammonium, stearyl trimethyl ammonium, tetrapropylammonium, hexadecyl ethyl ammonium, tetrapropylammonium, tetra-n-butylammonium, and combinations thereof. Additionally or alternatively, the catalyst may include or be formed from anions including, e.g., $ClO_3^-$, $NO_3^-$, $Br^-$, $CN^-$, $BrO_3^-$, $NO_2^-$, $HSO_4^-$, $HCO_3^-$, $SO_4^{2-}$, $CO_3^{2-}$, $PO_4^{3-}$, Toluenesulfonic acid ion, benzoic acid ion, ethanoic acid ion, or combinations thereof. While it is not particularly limited, it is preferred that the amount of the quaternary ammonium bases (quaternary ammonium salts thereof) be not less than 0.003 mol per mol of the phenolic hydroxyl group. It is believed that with an amount of less than 0.003 mol of quaternary ammonium bases per mol of phenolic hydroxyl group, the effect of reducing hydrolyzable chlorine is insufficient.

Examples of onium salts that may be used include tetramethylammonium chloride, tetraethylammonium chloride, tetrabutylammonium chloride, hexadecyl-trimethylammonium chloride, tetramethylammonium bromide, tetraethylammonium bromide, tetrabutylammonium bromide, hexadecyl-trimethylammonium bromide, tetraphenylphosphonium chloride, triphenyl-methylphosphonium chloride, triphenyl-ethylphosphonium chloride, triphenyl-propylphosphonium chloride, triphenyl-butylphosphonium chloride, benzyltriphenylphosphonium chloride, tetraphenylphosphonium bromide, triphenyl-metylphosphonium bromide, triphenyletylphosphonium bromide, triphenyletylphosphonium iodide, triphenybutylphosphonium iodide, benzyltriphenylphosphonium iodide, benzyltrimethylammonium chloride, benzyltrimethylammonium bromide, benzyltrimethylammonium hydroxide, benzyltriethylammonium chloride, benzyltriethylammonium bromide, tetrabutylammonium chloride, tetrabutylammonium bromide, tetrabutylammonium hydroxide, tetrabutylammonium hydrogen sulfite, tetraoctylammonium chloride, tetramethylammonium bromide, tetrabutylphosphonium chloride, tetrabutylphosphonium bromide, tetrabutylphosphonium iodide, ethyltriphenylphosphonium chloride, ethyltriphenylphosphonium bromide, ethyltriphenylphosphonium iodide, benzyltributylammonium chloride, trioctylmethylammonium chloride, chlorine chloride, and combinations thereof. Suitable onium salts include, but are not limited to, benzyltrimethylammonium chloride, benzyltriethylammonium chloride, tetraethylammonium chloride, and combinations thereof. In some instances, the catalyst is chosen from or includes benzy-triethylammonium chloride, benzy-trimethylammonium chloride, or combinations thereof.

The catalyst (e.g., onium salt) may be present in an amount of 1,000 to 9,000 ppm relative to the total amount of mono or polyhydric phenol. It is generally believed, that too much of an amount of catalyst may result in color deepening, while too little of an amount of catalyst may lower the reaction efficiency. For example, the catalyst may be present in an amount of about 1,500 to about 8,500 ppm, about 2,000 to about 7,000 ppm, about 2,500 to about 6,500 ppm, or about 3,000 ppm to about 6,000 ppm relative to the total amount of mono or polyhydric phenol. Additionally or alternatively, the catalyst may be present in an amount of about 1,000 to about 12,000 ppm relative to the amount of hydroxyl groups. In some instances, the amount of catalyst relative to the amount of hydroxyl groups may be from about 1,500 to about 9,500 ppm, about 2,000 to about 9,000 ppm, about 2,500 to about 8,500 ppm, about 3,000 to 8,000 ppm.

The produced halohydrin ether may, optionally, be a corresponding propylenechlorohydrin ether of a mono or polyhydric phenol. The reaction between ECH and a mono or polyhydric phenol may produce a product according to the following equation:

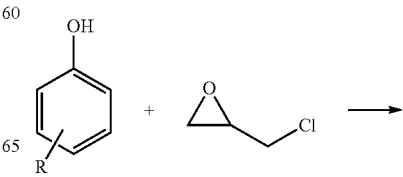

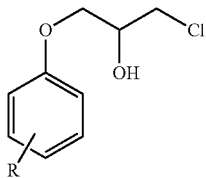

In some instances, R is a hydrogen, alkyl, aryl, (hydroxyar)alkyl, (hydroxyar)thiol or bis(hydroxyar)alkyl. The propylenechlorohydrin ether may in turn react with a second equivalent of epichlorohydrin to produce a minor amount of 1,3-dichloropropanol and the glycidyl ether of the phenol.

In step 120, the halohydrin ether is dehalogenated to form product of glycidyl ether of a mono or polyhydric phenol. The halohydrin ether may be dehalogenated using a base. The base is selected from an alkali metal or alkaline earth metal hydroxide, carbonate, bicarbonate, and a combination thereof. For example, the base may include one or more of NaOH, KOH, LiOH, $Ca(OH)_2$, $Ba(OH)_2$, $Mg(OH)_2$, $Mn(OH)_2$, $Na_2CO_3$, $K_2CO_3$, $Li_2CO_3$, $CaCO_3$, $BaCO_3$, $Mg_2CO_3$, $MnCO_3$, $NaHCO_3$, $KHCO_3$, $MgHCO_3$, $LiHCO_3$, $Ca(HCO_3)_2$, $Ba(HCO_3)_2$, $Mn(HCO_3)_2$, or combinations thereof. In some instances, the base is selected from NaOH, KOH, $Na_2CO_3$, $K_2CO_3$, and a combination thereof. The base may be a solid, liquid, or be in an aqueous solution. If the base is aqueous, the weight ratio of the base relative to the aqueous solution may be from 30 to 70 wt. %, or from 45 to 55 wt. %. The molar ratio of the base to the phenolic hydroxy group may be from 0.8:1 to 2:1, preferably from 0.85:1 to 1.5:1, or preferably from 0.8:1 to 1.2:1.

Additionally, in step 120, water and ECH are recovered by azeotropic distillation, e.g., during dehalogenation. The azeotrope of water and ECH may be condensed and subsequently into an organic phase and an aqueous phase using equipment and processes readily known by person of ordinary skill in the art in view of the Examples discussed below. The organic phase may be recycled into the reaction system. Preferably, the aqueous phase is discarded.

In step 130, unreacted ECH is removed under reduced pressure. Preferably, the crude glycidyl ether is dissolved in a solvent.

In step 140, the crude glycidyl ether solution is washed off with water. The solvent is distilled from the resulting mixture under reduced pressure to obtain the glycidyl ether.

Accordingly to another aspect of the disclosure, provided is a product of glycidyl ether of a mono or polyhydric phenol. The product of glycidyl ether of a mono or polyhydric phenol typically comprise an epoxy equivalent weight ("EEW") and a hydroxyl value ("HV"), wherein the epoxy equivalent weight multiplied by the hydroxyl value (EEW×HV) is a value from 1 to 10. For example, the product of glycidyl ether of a mono or polyhydric phenol may have a value for EEW×HV of 1 to 9, 1.5 to 9, 2 to 9, 2.5 to 9, or 3 to 9; 1 to 8.5, 1.5 to 8.5, 2 to 8.5, 2.5 to 8.5, or 3 to 8.5; 1 to 8, 1.5 to 8, 2 to 8, 2.5 to 8, or 3 to 8; 1 to 7.5, 1.5 to 7.5, 2 to 7.5, 2.5 to 7.5, or 3 to 7.5; or 1 to 7, 1.5 to 7, 2 to 7, 2.5 to 7, or 3 to 7.

The product of glycidyl ether of a mono or polyhydric phenol may have a value for EEW that is 150 to 200 g/eq and/or a value for HV that is from 0.01 to 0.06 eq/100 g. In some instances, the EEW value is from 150 to 200 g/eq, 155 to 200 g/eq, 160 to 200 g/eq, or 165 to 200 g/eq; from 150 to 195 g/eq, 155 to 195 g/eq, 160 to 195 g/eq, or 165 to 195 g/eq; or from 150 to 190 g/eq, 155 to 190 g/eq, 160 to 190 g/eq, or 165 to 190 g/eq; or from 150 to 185 g/eq, 155 to 180 g/eq, 160 to 185 g/eq, or 165 to 185 g/eq. The HV value may be from 0.01 to 0.06 eq/100 g, 0.02 to 0.06 eq/100 g, 0.03 to 0.06 eq/100 g; from 0.01 to 0.05 eq/100 g, 0.02 to 0.05 eq/100 g, 0.03 to 0.05 eq/100 g; or from 0.01 to 0.04 eq/100 g, 0.02 to 0.04 eq/100 g, 0.03 to 0.04 eq/100 g.

The product of glycidyl ether of a mono or polyhydric phenol may comprise 0.0001 to 0.11 mEq/g of alpha-glycol glyceryl ether groups. For example, the amount of alpha-glycol glyceryl ether groups may be from 0.0001 to 0.11 mEq/g, 0.001 to 0.11 mEq/g, 0.01 to 0.11 mEq/g, 0.05 to 0.11 mEq/g; from 0.0001 to 0.9 mEq/g, 0.001 to 0.9 mEq/g, 0.01 to 0.9 mEq/g, 0.05 to 0.9 mEq/g; from 0.0001 to 0.7 mEq/g, 0.001 to 0.7 mEq/g, 0.01 to 0.7 mEq/g, 0.05 to 0.7 mEq/g; from 0.0001 to 0.5 mEq/g, 0.001 to 0.5 mEq/g, 0.01 to 0.5 mEq/g; or from 0.0001 to 0.3 mEq/g, 0.001 to 0.3 mEq/g, 0.01 to 0.3 mEq/g. Additionally or alternatively, the product of glycidyl ether of a mono or polyhydric phenol may include 300 ppm or less of hydrolyzable chlorine. In some instances, the amount of hydrolyzable chlorine present in the product of glycidyl ether of a mono or polyhydric phenol is preferably 280 ppm or less, preferably 260 ppm or less, preferably 240 ppm or less, preferably 220 ppm or less, preferably 200 ppm or less, preferably 180 or less, preferably 160 or less, preferably 140 or less, preferably 120 or less, or preferably 100 or less.

The product of glycidyl ether of a mono or polyhydric phenol may be formed from monohydric phenols, polyhydric phenols or phenolic resins. The phenolic compounds can be obtained from biological or chemical conversions. Useful phenolic compounds include, for example, phenol, o-cresol, m-cresol, p-cresol, p-tert-butylphenol, p-tert-octylphenol, p-phenylphenol, p-cumylphenol, p-isopropylphenol, p-nonylphenol, 2,3-dimethylphenol, 2,4-dimethylphenol, 2,5-dimethylphenol, 2,6-dimethylphenol, 3,4-dimethylphenol, 3,5-dimethylphenol, o-ethylphenol, m-ethylphenol, p-ethylphenol, 2,3,4-trimethylphenol, 2,3,5-trimethylphenol, 3,4,5-trimethylphenol, cardanol, and guaiacol, or mixtures thereof.

The phenol used to produce the product of glycidyl ether of a mono or polyhydric phenol may be substituted or unsubstituted bisphenol compounds, for example, bisphenol, 2,2-Bis(4-hydroxyphenyl)propane (Bisphenol A), 1,1-Bis(4-hydroxyphenyl)-1-phenyl-ethane (Bisphenol AP), 2,2-Bis(4-hydroxyphenyl)hexafluoropropane (Bisphenol AF), 2,2-Bis(4-hydroxyphenyl)butane (Bisphenol B), Bis-(4-hydroxyphenyl)diphenylmethane (Bisphenol BP), 2,2-Bis(3-methyl-4-hydroxyphenyl)propane (Bisphenol C), Bis (4-hydroxyphenyl)-2,2-dichlorethylene (Bisphenol C2), 1,1-Bis(4-hydroxyphenyl)ethane (Bisphenol E), Bis(4-hydroxyphenyl)methane (Bisphenol F), 2,2-Bis(4-hydroxy-3-isopropyl-phenyl)propane (Bisphenol G), 1,3-Bis(2-(4-hydroxyphenyl)-2-propyl)benzene (Bisphenol M), Bis(4-hydroxyphenyl)sulfone (Bisphenol S), 1,4-Bis(2-(4-hydroxyphenyl)-2-propyl)benzene (Bisphenol P), 5,5'-(1-Methylethyliden)-bis[1,1'-(bisphenyl)-2-ol]propane (Bisphenol PH), 1,1-Bis(4-hydroyphenyl)-3,3,5-trimethyl-cyclohexane (Bisphenol TMC), 1,1-Bis(4-hydroxyphenyl)-cyclohexane (Bisphenol Z), tetramethyl bisphenol A, tetramethyl bisphenol F, tetramethyl bisphenol S, tetramethyl bisphenol Z, halogenated bisphenol A, tetrabrominated bisphenol A, tetrachlorinated bisphenol A, dihydroxy diphenyl sulfide, 4,4-thiobis (3-methyl-6-tert-butylphenol), or mixtures thereof.

In some instances, the phenol for producing the product of glycidyl ether of a mono or polyhydric phenol is an unsubstituted diphenol compounds. Substituted or unsubstituted diphenol compounds may be, for example, catechol, resorcinol, methylresorcinol, hydroquinone, monomethyl hydroquinone, dimethyl hydroquinone, trimethyl hydroquinone, mono-tert-butyl hydroquinone, di-tert-butyl hydroquinone, dihydroxy naphthalene, dihydroxy methyl naphthalene, and dihydroxy methyl naphthalene, or mixtures thereof.

The product of glycidyl ether of a mono or polyhydric phenol may be formed from raw materials or compounds obtained from the reaction of phenolic compounds with aldehydes. The aldehydes that may be used to form phenolic compounds or raw materials include, for example, formaldehyde, acetaldehyde, propionaldehyde, butyraldehyde, valeraldehyde, hexanal, benzaldehyde, chloral, bromoaldehyde, glyoxal, malondialdehyde, succinaldehyde, glutaraldehyde, adipaldehyde, cyclohexanal, terpaldehyde, acrolein, crotonaldehyde, salicylaldehyde, furfural, hydroxybenzaldehyde, fumaraldehyde, hexa-2,4-dienedial, octa-2,4,6-trienedial, phenylglyoxal, terephthalaldehyde, phthalaldehyde, isophthalaldehyde, naphthalene dicarbaldehyde, or mixtures thereof. Useful phenolic resins include, for example, phenol novolak, brominated phenol novolak, o-cresol novolak, resorcin novolak, brominated resorcin novolak, tris(hydroxyphenyl)methane, tetraphenol ethane phenolic resin, or combinations thereof. Additional phenolic resins include the aldehyde-polyphenolic condensates of U.S. Pat. No. 10,138,325 B2, the dicyclopentadiene-phenolic resins in European Patent no. 0148817, and 9,10-dihydro-9-oxa-10-phosphaphenanthrene-10-oxide (DOPO) phenolic resins of U.S. Pat. Nos. 6,984,716 and 8,426,547, all of which are incorporated herein in their entirety for all purposes.

In certain instances, the product of glycidyl ether of a mono or polyhydric phenol may be formed from a polyhydric phenol that is selected from resorcinol, hydroquinone, 2,2-bis-(4'-hydroxyphenyl)-propane (bisphenol A), mixtures of isomers of 2,2', 2,4' and 4,4'dihydroxydiphenyl methane (bisphenol F), 4,4'-di-hydroxydiphenyl cyclohexane, 4,4'-dihydroxy-3,3'-dimethyldiphenyl propane, 4,4'-dihydroxydiphenyl, 4,4'-dihydroxybenzophenone, bis-(4'-hydroxyphenyl)-1,1-ethane, bis-(4'-hydroxyphenyl)-1,1-isobutane, bis-(4'-hydroxy-tert.-butylphenyl)-2,2-propane, bis-(2-hydroxy-naphthyl)-methane, 1,5-dihydroxynaphthalene, tris-(4-hydroxyphenyl)-methane, and bis-(4-hydroxy-phenyl) ether, bis-(4-hydroxyphenyl) sulfone, phenol novolak, brominated phenol novolak, o-cresol novolak, resorcin novolak, brominated resorcin novolak, tris(hydroxyphenyl)methane, tetraphenol ethane phenolic resin, aldehyde-polyphenolic condensates, dicyclopentadiene-phenolic resins, 9,10-dihydro-9-oxa-10-phosphaphenanthrene-10-oxide (DOPO) phenolic resins, and a combination thereof.

The product of glycidyl ether of a mono or polyhydric phenol may be formed from a epihalohydrins selected from epichlorohydrin, epibromohydrin, epiiodohydrin, methylepichlorohydrin, methylepibromohydrin, methylepiiodohydrin and combinations thereof. The source of the epihalohydrins may be fresh or recycleded epihalohydrin, such as those isolated in step 140. The epihalohydrins may have impurities including, e.g., water, the solvent used in the reaction, glycidol, glycerol, 1-halo-propanol, 2-halo-propanol, 2-halo-allylacohol, 1,3-dihalo-2-propanol, 2,3-dihalo-2-propanol, and 1-halo-2,3-propanediol.

As noted above, the product of glycidyl ether of a mono or polyhydric phenol preferably has a molar ratio of the ECH to the phenolic hydroxy group ([ECH]/[OH]) that is 3.5:1 to 11.0:1. In some instances, the molar ratio of the ECH to the phenolic hydroxy group(s) ([ECH]/[OH]) is from 3:5 to 10.9:1, 3.7:1 to 11:1, 4:1 to 10.74:1, 4:1 to 10:1, 4:1 to 9:1, 4:1 to 8:1, 4.5:1 to 10.74:1, 4.5:1 to 10:1, 4.5:1 to 9:1, or 4.5:1 to 8:1.

The product of glycidyl ether of a mono or polyhydric phenol of the present disclosure may be produced using a solvent during the reaction to dissolve reactants or may be produced without a solvent. The amount of the solvent may vary but is typically present in an amount of 20 parts to 95 parts by weight relative to the solid content. In some examples, the amount of solvent present in the epoxy is 30 parts to 90 parts, 40 parts to 85 parts, or 50 parts to 80 parts, by weight relative to the solid content.

The solvent which can be used herein is not particularly limited as long as it is an inert solvent for the carboxylic acid esterification reaction. The solvent may be an aliphatic hydrocarbon solvents, an ester solvent, an ether solvent, an organic solvent, and/or a ketone solvent. Examples of solvents include toluene, xylene, ethylbenzene, and tetramethylbenzene, hexane, octane, decane, petroleum ether, white gasoline, solvent naphtha, or combinations thereof. Suitable ester solvents include alkyl acetates, such as ethyl acetate, propyl acetate and butyl acetate; cyclic esters, such as y-butyrolactone; ethylene glycol monomethyl ether acetate, diethylene glycol, methyl ether monoacetate, diethylene glycol monoethyl ether monoacetate, triethylene glycol monoethyl ether; monoalkylene glycol monoalkyl ether monoacetate, such as monoacetate, diethylene glycol monobutyl ether monoacetate, propylene glycol monomethyl ether acetate, and butanediol monomethyl ether acetate; and/or polyalkylene glycol monoester, such as a monoalkyl ether monoacetate, dialkyl glutarate, dialkyl succinate, and dialkyl adipate.

Examples of the ether solvent include alkyl ethers, such as diethyl ether and ethylbutyl ether; glycol ethers, such as ethylene glycol dimethyl ether, ethylene glycol diethyl ether, dipropylene glycol dimethyl ether, dipropylene glycol diethyl ether, triethylene glycol dimethyl ether, triethylene glycol diethyl ether; and cyclic ethers, such as tetrahydrofuran. Suitable ketone solvent include acetone, methyl ethyl ketone, methyl propyl ketone, methyl isobutyl ketone, cyclohexanone, and/or isophorone.

The solvent, if present, may be an organic solvent selected from an alcohols, such as primary alcohols, secondary alcohols, ethanol, 1-propanol, 1-butanol, 1-pentanol and 1-hexanol, isopropanol, 2-butanol, 2-pentanol, 3-pentanol, 2-hexanol, cyclohexanol, 2-heptanol, 3-heptanol, tert-butanol, tert-pentanol. Examples of other organic solvent include ethylene glycol, ethylene glycol monomethyl ether, ethylene glycol monoethyl ether, ethylene glycol mono-n-propyl ether, ethylene glycol monobutyl-n-butyl ether, ethylene glycol monophenyl ether, diethylene glycol, diethylene glycol monomethyl ether, diethylene glycidyl, monoethyl ether, diethylene glycol mono-n-propyl ether, diethylene glycol mono-n-butyl ether, triethylene glycol, triethylene glycol monomethyl ether, triethylene glycol-monobutyl n-butyl ether, propylene glycol, propylene glycol monomethyl ether, propylene glycol mono ethyl ether, propylene glycol mono-n-propyl ether, propylene glycol mono-n-butyl ether, propylene glycol monophenyl ether, dipropylene glycol, dipropylene glycol monomethyl ether, dipropylene glycol monoethyl ether, dipropylene glycol mono-n-propyl ether, dipropylene glycol mono-n-butyl Ether, tripropylene glycol, tripropylene glycol monomethyl ether and tripropylene glycol, such as mono-n-butyl ether. In at least one instance, the organic solvents are chosen from aliphatic and aromatic hydrocarbons, aliphatic secondary alcohols, halogenated aliphatic hydrocarbons, aliphatic ethers, aliphatic nitriles, cyclic ethers, ketones, amides, sulfoxides, and combinations thereof, such as pentane, hexane, octane, toluene, xylene, methylethylketone, methylisobutylketone, N,N-dimethylformamide, dimethylsulfoxide, tetrahydrofuran, 1,4-dioxane, dichloromethane, ethylene glycol dimethyl ether, N,N-dimethylacetamide, acetonitrile, isopropanol, isobutanol, propylene glycol monomethyl ether, and combinations thereof.

In accordance with a further aspect of the disclosure, provided is an epoxy resin composition comprising a hardener and the product of glycidyl ether of a mono or polyhydric phenol disclosed herein. The hardener may be selected from polyetheramine, Isophoronediamine, 4,4-Diaminodicyclohexylmethane, 4,4'-methylenebis(2-methylcyclohexyl-amine), 4-methyl-1,3'-cyclohexanediamine, Dicyandiamide, imidazoles, phenol novolak, diaminodiphenylmethane, diaminodiphenylsulfone, m-phenylenediamine, phthalic anhydride, tetrahydrophthalic anhydride, pyrromellitic anhydride, benzophenone tetracarboxylic anhydride, and a combination thereof.

The hardener may be selected and/or the amount of such hardener controlled such that the epoxy resin composition after curing has a glass transition temperature of more than 137° C. In some instances, the glass transition temperature is more than 138° C., more than 139° C., more than 140° C., more than 141° C., more than 142° C., more than 143° C., more than 144° C., more than 145° C., more than 146° C., more than 147° C., more than 148° C., more than 149° C., more than 150° C., more than 151° C., or more than 152° C. In at least one instance, the hardener is isophoronediamine and the glass transition temperature of the epoxy resin composition after curing is more than 137° C. Additionally or alternatively, the hardener may be selected and/or the amount of such hardener controlled such that the epoxy resin composition after curing has a viscosity pot life of 40 to 100 minutes at a temperature of 30° C. For example, the viscosity pot life, at a temperature of 30° C., may be from 40 to 100 minutes, 45 to 100 minutes, 50 to 100 minutes, 55 to 100 minutes, 60 to 100 minutes, 70 to 100 minutes, or 75 to 100 minutes; from 40 to 85 minutes, 45 to 85 minutes, 50 to 85 minutes, 55 to 85 minutes, 60 to 85 minutes, 70 to 85 minutes, or 75 to 85 minutes; or from 40 to 75 minutes, 45 to 75 minutes, 50 to 75 minutes, 55 to 75 minutes, or 60 to 75 minutes. In certain instances, the hardener is isophoronediamine and the viscosity pot life of the epoxy resin, at a temperature of 30° C., is from 40 to 100 minutes.

EXAMPLES

The following Examples are provided primarily for the purpose of elucidating the benefits and advantages achieved by aspects of the invention.

Examples 1-3 and Comparative Examples 1-4

In Examples 1-3, glycidyl ethers of 4,4'-(propane-2,2-diyl)diphenol were produced from 4,4'-(propane-2,2-diyl)diphenol (hereafter "BPA"), which were obtained from Chang Chun Plastic. Comparative glycidyl ethers of BPA were produced in accordance with Comparative Examples 1-4. The properties of the glycidyl ethers of BPA produced by Examples 1-3 and Comparative Examples 1-4 are provided in Table 1, which follows below.

Example 1

Glycidyl ether of BPA was produced using a 3 L-4-neck reactor that was equipped with a device for controlling and displaying the temperature and pressure as well as a device for condensing a co-distillation mixture of water and epichlorohydrin (also referenced herein as "ECH"), and separating the co-distillation mixture into an organic phase and an aqueous phase. Specifically, 300 grams (hereafter "g") of BPA and 900 g of ECH were added in the 3 L-4-neck reactor with 2.7 g of benzyltriethylammonium chloride (9,000 ppm to BPA), which acted as a catalyst for the coupling step. The ratio of the ECH to the OH groups from BPA was 3.7 ([ECH]/[OH]=3.7). The purity of the epichlorohydrin was over 99 wt. %, and the contents of glycidol and water in epichlorohydrin were 0.31 wt. % and 0.15 wt. % respectively. The mixture was stirred to form a homogeneous solution under atmospheric pressure at 40° C. and the temperature was gradually raised from 40° C. to 75° C. over 50 hours, then the temperature was maintained at 75° C. for another 16 hours.

A first dehydrohalonation step was then performed by adding 205 g of 49.5 wt. % aqueous sodium hydroxide solution to the mixture at a constant rate for 6 hours at a temperature of 60° C. while water contained in the reaction system was azeotropically distillated and condensed under an absolute pressure of 100 torr. The condensed azeotrope was separated into an organic phase and an aqueous phase. The organic phase (ECH mainly) was recycled back into the reactor and the aqueous phase was discarded. After completing the addition of the 205 g of sodium hydroxide solution (49.5%), the system was maintained at the same conditions for an hour. The first dehydrohalonation step was completed, and unreacted ECH was distillated off under a reduced pressure.

An additional dehydrohalonation step was performed by adding 4.0 g of 49.5% aqueous sodium hydroxide solution at a temperature of 80° C. for 2 hours under atmospheric pressure. Subsequently, sodium chloride contained in the resulting crude epoxy resin was dissolved in toluene and deionized water and washed off with water. The organic solvent was distillated from the resulting mixture under reduced pressure to obtain the glycidyl ether.

Example 2

Glycidyl ether of BPA was synthesized using the same procedure described in Example 1, except that: the amount of epichlorohydrin employed was 1,120 g; the ratio of the ECH to the OH groups from BPA was 4.61 ([ECH]/[OH]=4.61); the contents of glycidol and water in epichlorohydrin were 0.44 wt. % and 0.04 wt. % respectively, and the amount of benzyltriethylammonium chloride was 1.35 g (4,500 ppm to BPA).

Example 3

Glycidyl ether of BPA was synthesized in the same procedure as that in the Example 1, except that: the amount of epichlorohydrin was 1,650 g; the ratio of the ECH to the OH groups from BPA was 6.79 ([ECH]/[OH]=6.79); the contents of glycidol and water in epichlorohydrin were 0.15 wt. % and less than 0.01 wt. % respectively; and the amount of benzyltriethylammonium chloride was 0.6 g (2,000 ppm to BPA).

Example 4

Glycidyl ether of BPA was synthesized in the same procedure as that in the Example 1, except that: the amount of epichlorohydrin was 850 g; the ratio of the ECH to the OH groups from BPA was 3.5 ([ECH]/[OH]=3.5); the contents of glycidol and water in epichlorohydrin were 0.15 wt. % and less than 0.01 wt. % respectively; the amount of benzyltriethylammonium chloride was 1.2 g (4,000 ppm to BPA); and in the coupling step, the temperature was gradually raised from 45° C. to 60° C. over 48 hours, then the temperature was maintained at 60° C. for another 8 hours.

Comparative Example 1

Glycidyl ether of BPA was synthesized according to the procedures of U.S. Pat. No. 6,001,873, which is incorporated herein in its entirety for all purposes. For instance, 300 g of BPA, 680 g of epichlorohydrin and 100 g of isopropyl acetate were added to a 3 L-4-neck reactor equipped with a device for controlling and showing the temperature and pressure and a device for condensing co-distillation mixture of water. The ratio of the ECH to the OH groups from BPA was 2.8 ([ECH]/[OH]=2.8). Epichlorohydrin and the solvents were separated into an organic phase and an aqueous phase.

The mixture was stirred to form a homogeneous solution under atmospheric pressure and then heated to 70° C. under an absolute pressure of 60 mm Hg. After reaching equilibrium of the pressure and the temperature, 205 g of 49.5 wt. % aqueous sodium hydroxide solution was added to the mixture at a constant rate over 5 hours while water contained in the reaction system was azeotropically distilled and condensed. The condensed azeotrope was separated into an organic phase and an aqueous phase. The organic phase (ECH mainly) was sequentially recycled into the reaction system and the aqueous phase was discarded. After the reaction had completed, unreacted epichlorohydrin and the solvent were distillated off under reduced pressure. Sodium chloride contained in the resulting crude glycidyl ether mixture was dissolved in toluene and deionized water and washed off with water. The organic solvent was distilled from the resulting mixture under reduced pressure to obtain the glycidyl ether of BPA.

Comparative Example 2

Glycidyl ether of BPA was synthesized according to the procedure described in the Example 2, except that: the amount of epichlorohydrin was 730 g; the ratio of the ECH to the OH groups from BPA was 3.0 ([ECH]/[OH]=3.0); and the contents of glycidol and water in ECH were 0.65% and 1.34% respectively.

Comparative Example 3

Comparative Example 3 is D.E.R.™ 330, which was a commercially obtained glycidyl ether of BPA produced by Olin (Dow Chemical).

Comparative Example 4

Comparative Example 4 is D.E.R.™ 332, which was a commercially obtained glycidyl ether of BPA produced by Olin (Dow Chemical).

TABLE 1

|  | Ex. 1 | Ex. 2 | Ex. 3 | Ex. 4 | Comp. Ex. 1 | Comp. Ex. 2 | Comp. Ex. 3 | Comp. Ex. 4 |
| --- | --- | --- | --- | --- | --- | --- | --- | --- |
| [ECH]/[OH] | 3.70 | 4.61 | 6.79 | 3.50 | 2.80 | 3.00 | — | — |
| Catalyst (ppm) | 9,000 | 4,500 | 2,000 | 4,000 | — | 4,500 | — | — |
| EEW (g/eq) | 180.5 | 177.9 | 173.3 | 175.7 | 185.6 | 181.2 | 179.8 | 177.6 |
| HyCl (ppm) | 84 | 70 | 93 | 48 | 139 | 441 | 175 | 244 |
| Viscosity (mPa · s) | 8,210 | 6,430 | 4,880 | 7,080 | 12,460 | 9,650 | 8,650 | 4,920 |
| α-glycol (mEq/g) | 0.0105 | 0.0025 | 0.0007 | 0.0018 | 0.0361 | 0.0090 | 0.0145 | 0.0110 |
| HPLC n = 0 (%) | 88.2 | 91.2 | 94.3 | 89.0 | 78.4 | 84.3 | 88.7 | 91.2 |
| HPLC GE (%) | 0.956 | 1.784 | 2.512 | 1.122 | 0.511 | 0.186 | 0.852 | 0.440 |
| HV value (eq/100g) | 0.048 | 0.035 | 0.013 | 0.044 | 0.069 | 0.071 | 0.065 | 0.061 |
| EEW × HV (eq/eq) | 8.66 | 6.23 | 2.25 | 7.73 | 12.81 | 12.87 | 11.69 | 10.83 |

Examples 1-4 and Comparative Examples 1-4 were assessed to determine the Hydrolyzable chlorine (herein "HyCl") according to the method of ASTM D1652. The viscosity (herein "VIS") of Examples 1-4 and Comparative Examples 1-4 were assessed according to the method of ISO 3219. The epoxy equivalent weight (herein "EEW") was determined according to the method of ASTM D1652.

The hydroxyl value (herein "HV value") according to the method of ASTM E222 (Method C) and using the calculation shown below:

$$\text{Hydroxyl value}(eq/100g) = \frac{(V_0 - V_s) \times C}{10 \times W} - 2 \times \frac{100}{EEW}$$

where:
C=0.5 meq/mL, NaOH standard solution,
EEW=Epoxy equivalent weight (g/eq) of the sample,
$V_O$=mL of the NaOH standard solution required for the blank test,
$V_S$=mL of the NaOH standard solution required for the sample, and
W=gram of the sample used.

HPLC analysis was conducted on Examples 1-4 and Comparative Examples 1-4 using a Waters 600 apparatus, a Waters 2487 Dual λ Absorbance Detector, and a Waters XTerra RP18 4.6 mm×250 mm 5 um Column. The detect wavelength used was 254 nm; the column temperature was 40° C.; the mobile phase was a solution of water and acetonitrile at a ratio of 40:60 to 0:100 (v.v) over 80 mins; and the flow rate of mobile phase was 1.0 mL/min.

As shown in the Table 1, Examples 1-4 have a low α-glycol and a low HV value. Additionally, Examples 1-4 have high contents of n=0 and MGE (multiple glycidyl ethers, Strusture (III)). Referring to the structure shown below, the higher the amount of n=0, the lower the EEW, which indicates a higher purity of the product of glycidyl ethers.

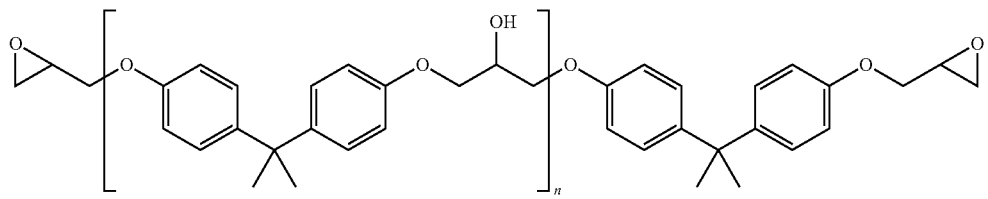

The above structure is a theoretical representation of the BPA diglycidyl ether structure and, as noted above, numerous compounds having varying structures similar to the one theoretical representation presented above are produced during the actual methods for forming products of glycidyl ethers of mono or polyhydric phenol. Examples 1-4 beneficially had a product value of EEW and HV (EEW×HV), which is the ratio of OH group to glycidyl ether group, of less than 10. Conversely, Comparative Examples 1-4 had a product value of EEW and OH of greater than 10. The inventors recognized that typically the higher the value for ECH to the phenolic hydroxy group ([ECH]/[OH]) is, the more MGE compounds and the less OH groups in the product. For example, a greater value for [ECH]/[OH] may indicate more MGE compounds, Structure (III), and a lower EEW value. A greater value for [ECH]/[OH] may also indicate a lesser amount of hydroxyl groups and lower HV value. The inventors discovered that an increase in the value of [ECH]/[OH] may decrease or correlate to a decrease in the value of EEW×HV.

Examples 5-7 and Comparative Examples 5-7

In Examples 5-7, glycidyl ethers of Bisphenol F from Bisphenol F (hereafter "BPF"), which were obtained from Chang Chun Plastic. Comparative glycidyl ethers of BPF were produced in accordance with Comparative Examples 5-7. The properties of the glycidyl ethers produced by Examples 5-7 and Comparative Examples 5-7 are provided in Table 2, which is provided below.

Example 5

Glycidyl ether of BPF was synthesized according to the procedure described in Example 1, except that BPF having a dimer content of 85.2% (obtained from Chang Chun Plastic) was used to prepare the glycidyl ethers instead of the BPA used in Example 1. Additionally, the amount of epichlorohydrin used was 1,360 g. The ratio of the ECH to the OH groups from BPF was 4.88 ([ECH]/[OH]=4.88). The contents of glycidol and water in the epichlorohydrin were 0.12 wt. % and less than 0.01 wt. % respectively. The amount of benzyltriethylammonium chloride used was 1.35 g (4,500 ppm to BPF), and amount of 49.5 wt. % aqueous sodium hydroxide solution used was 240 g.

Example 6

Glycidyl ether of BPF was synthesized according to the procedure described in Example 5, except that: the amount of epichlorohydrin used was 1,850 g, the ratio of the ECH to the OH groups from BPF was 6.33 ([ECH]/[OH]=6.33); the amount of benzyltriethylammonium chloride used was 0.45 g (1,500 ppm to BPF); and the amount 49.5 wt. % aqueous sodium hydroxide solution used was 255 g.

Example 7

Glycidyl ether of BPF was synthesized according to the procedure described in Example 5, except that the BPF having a dimer content of 85.2 wt. % was replaced with a BPF having a dimer content of 90.1 wt. %, which was obtained from Honshu Chemical.

Comparative Example 5

Glycidyl ether of BPF was synthesized in accordance with the procedure described in Example 5, except that the amount of epichlorohydrin was 836 g and the ratio of the ECH to the OH groups from BPF was 3.0 ([ECH]/[OH]=3.0).

Comparative Example 6

Glycidyl ether of BPF was synthesized in accordance with the procedure described in Comparative Example 1, except that: the BPA used in Comparative Example 1 was replaced with a BPF having a dimer content of 85.2%; the amount of epichlorohydrin was 1,360 g, the ratio of the ECH to the OH groups from BPF was 4.88 ([ECH]/[OH]=4.88); the content of glycidol and water in the epichlorohydrin was 0.12% and less than 0.01%, respectively; and the amount of 49.5% aqueous sodium hydroxide solution was 240 g. The procedure for produce this glycidyl ether of BPF did not include an onium salt catalyst.

Comparative Example 7

The property data of Comparative Example 7 is from example 1 of Japan Patent JP 2017/155080 A, which is incorporated herein in its entirety for all purposes. In example 1 of Japan Patent JP 2017/155080 A, a glass separable flask equipped with a reflux condenser, a stirrer, a nitrogen inlet pipe, and an oil-water separator and a vacuum device was used to produce bisphenol F type liquid resin. 100 parts of BPF-1, 231.3 parts of epichlorohydrin having a molar ratio ECH/OH=2.5 of epichlorohydrin per 1 mol of phenolic hydroxyl group of bisphenol F, and 1.6 parts of water were charged in the aforementioned equipment. The dimer (2 nuclide) content of the BPF-1 was 97.2%. The temperature was increased to 60° C. under a nitrogen atmosphere to dissolve the added components.

Next, while maintaining the temperature in the reaction system at 60° C., the reaction system was gradually reduced in pressure to azeotrope epichlorohydrin and water, the water was removed from the upper layer through an oil-water separator, and the lower layer of epichlorohydrin was returned to the system. While maintaining this state, 73.5 parts of 49% aqueous sodium hydroxide solution having a molar ratio NaOH/OH=0.9 of sodium hydroxide per 1 mol of phenolic hydroxyl group of bisphenol F was added drop wise over 150 minutes. During this time, the reaction system was maintained at a temperature of 60° C. to 65° C. while the degree of vacuum was held at about 100 to about 140 mmHg, and the water content in the system was 2.6 to 3.2%.

After completion of the drop wise addition, the refluxed epichlorohydrin was removed from the system and then the degree of pressure reduction and the temperature were gradually increased. The epichlorohydrin was recovered and removed at a temperature of 150° C. and a pressure of 5 mmHg to obtain a crude glycidyl ether. Thereafter, the reaction system was returned to normal pressure, and 300 parts of toluene was added to dissolve the crude glycidyl ether. Additionally, 10 parts of 20% aqueous sodium hydroxide solution was added to the crude glycidyl ether solution. The reaction was subsequently carried out at temperature of 80° C. for 1.5 hours. 500 parts of water was added to separate and remove the by-produced salt. Thereafter, washing was performed several times with 300 parts of water, and repeated until the washing water became neutral. This solution was heated to a temperature of 150° C. under a reduced pressure of 5 mmHg to remove toluene, thereby obtaining a bisphenol F type liquid resin.

prepared from a feed BPF that had a significantly higher amount of dimer structures than the feed BPF used to produce the glycidyl ethers of BPF from Examples 5 and 6.

Examples 8-10 and Comparative Examples 8-10

In Example 8, glycidyl ether of hydroxybenzaldehyde phenolic resin were produced using hydroxybenzaldehyde phenolic resin (hereafter "PF1250"), which was obtained from Chang Chun Plastic. In Example 9, glycidyl ether of glyoxal-phenol condensates were produced according to aspects of the disclosure. In Example 10, glycidyl ether of dicyclopentadiene phenol resin were produced using dicyclopentadiene phenol resin (hereafter "PF9110"), which was obtained from Chang Chun Plastic. Comparative Examples 8-10 were commercially available glycidyl ethers obtained from Chang Chun Plastic. The raw materials used for Comparative Examples 8-10 were consistent with Example 8-10 respectively. The properties of the glycidyl ethers of

TABLE 2

|  | Ex 5 | Ex 6 | Ex 7 | Comp. Ex. 5 | Comp. Ex. 6 | Comp. Ex. 7 |
|---|---|---|---|---|---|---|
| [ECH]/[OH] | 4.9 | 6.6 | 4.9 | 3.0 | 4.9 | 2.5 |
| BPF Dimer (GPC %) | 85.2 | 85.2 | 90.1 | 85.2 | 85.2 | 97.2 |
| EEW (g/eq) | 163.9 | 160.2 | 158.3 | 170.8 | 167.2 | 172 |
| HyCl (ppm) | 132 | 101 | 94 | 228 | 285 | 180 |
| Viscosity (mPa.s) | 2,520 | 1,960 | 1,620 | 3,650 | 3,320 | 3,720 |
| α-glycol (mEq/g) | 0.0052 | 0.0011 | 0.0053 | 0.0044 | 0.0225 | 0.038 |
| Dimer (GPC %) | 80.2 | 83.1 | 85.0 | 76.2 | 77.3 | 77.1 |
| HV value (eq/100 g) | 0.045 | 0.031 | 0.036 | 0.064 | 0.062 | — |
| EEW × HV (eq/eq) | 7.38 | 4.97 | 5.70 | 10.93 | 10.37 | — |

The amount of dimer structures in the glycidyl ethers of BPF of Examples 5-7 and Comparative Examples 5-6 were determined using gel-permeation chromatography. Specifically, a Waters 717 Autosampler and Waters 515 Pumps was used in conjunction with a Waters 2487 Dual λ Absorbance Detector for the gel-permeation chromatography. The detector wavelength was 254 nm and the detector temperature was 35° C.

As shown in Table 2, the glycidyl ethers of BPF from Examples 5-7 exhibited a low α-glycol, low OH value, and low viscosity. Further, the glycidyl ethers of BPF from Examples 5 and 6 had amount of dimer structures as determined from the gel-permeation chromatography. Notably, the glycidyl ethers of BPF from Examples 5 and 6 had a greater amount of dimer structures than the glycidyl ethers of BPF from Comparative Example 7, even though the glycidyl ethers of BPF from Comparative Example 7 was Examples 8-10 and Comparative Examples 8-10 are provided in Table 3, which is provided below.

Example 8

Glycidyl ether of PF1250 was synthesized in accordance with the procedure described in Example 2, except that: PF1250 was used instead of the BPA used in Example 2; the amount of epichlorohydrin was 1,850 g; the ratio of the ECH to the OH groups from PF1250 was 6.53 ([ECH]/[OH]=6.53); the contents of glycidol and water in the epichlorohydrin were 0.12 wt. % and less than 0.01 wt. % respectively; and the amount of 49.5 wt. % aqueous sodium hydroxide solution was 220 g.

An exemplary structure of a theoretical glycidyl ether of Example 8 and PF1250 is provided below to illustrate the core repeat unit of a theoretical glycidyl ether of Example 8.

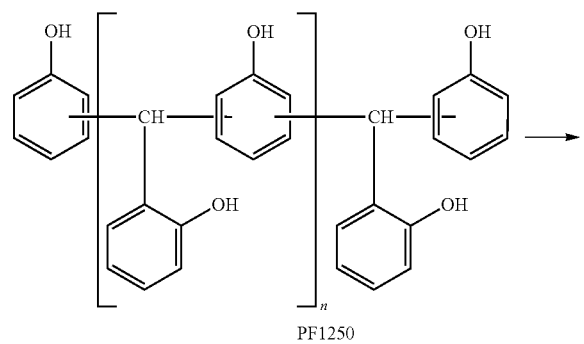

PF1250

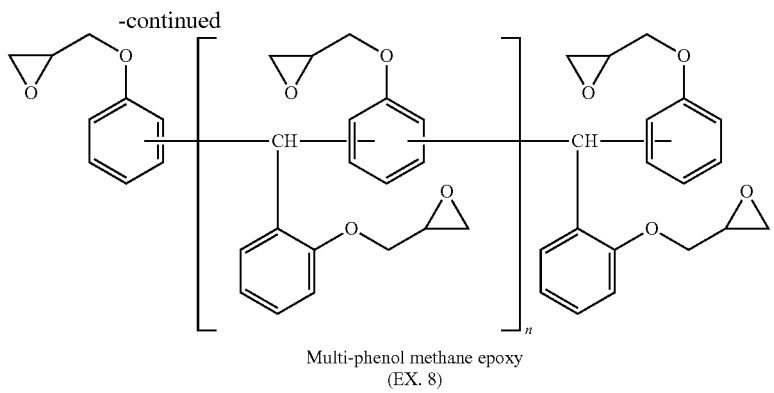

Multi-phenol methane epoxy
(EX. 8)

The above structure is a theoretical representation and, as noted above, numerous compounds having varying structures similar to the theoretical representation presented above are produced during the actual methods for forming products of glycidyl ethers of Example 8.

Example 9

Glycidyl ether of glyoxal-phenol condensates was synthesized in accordance with the procedure described in Example 2, except that glyoxal-phenol condensates were used instead of the BPA used in Example 2. The glyoxal-phenol condensates were synthesized according to the procedure described in Example 2 of U.S. Pat. No. 10,138,325.

Additionally, the amount of epichlorohydrin used in this Example was 1,480 g. The ratio of the ECH to the OH groups from glyoxal-phenol condensates was 6.67 ([ECH]/[OH]=6.67). The content of glycidol and water in the epichlorohydrin was 0.12 wt. % and less than 0.01 wt. % respectively. Further, during the coupling step, the temperature was increased from a starting point temperature of 50° C. The amount of 49.5 wt. % aqueous sodium hydroxide solution was 190 g.

An exemplary structure of a theoretical glycidyl ether of Example 9 and multi-phenol ethane novolac is provided below to illustrate the core repeat unit of a theoretical glycidyl ether of Example 9.

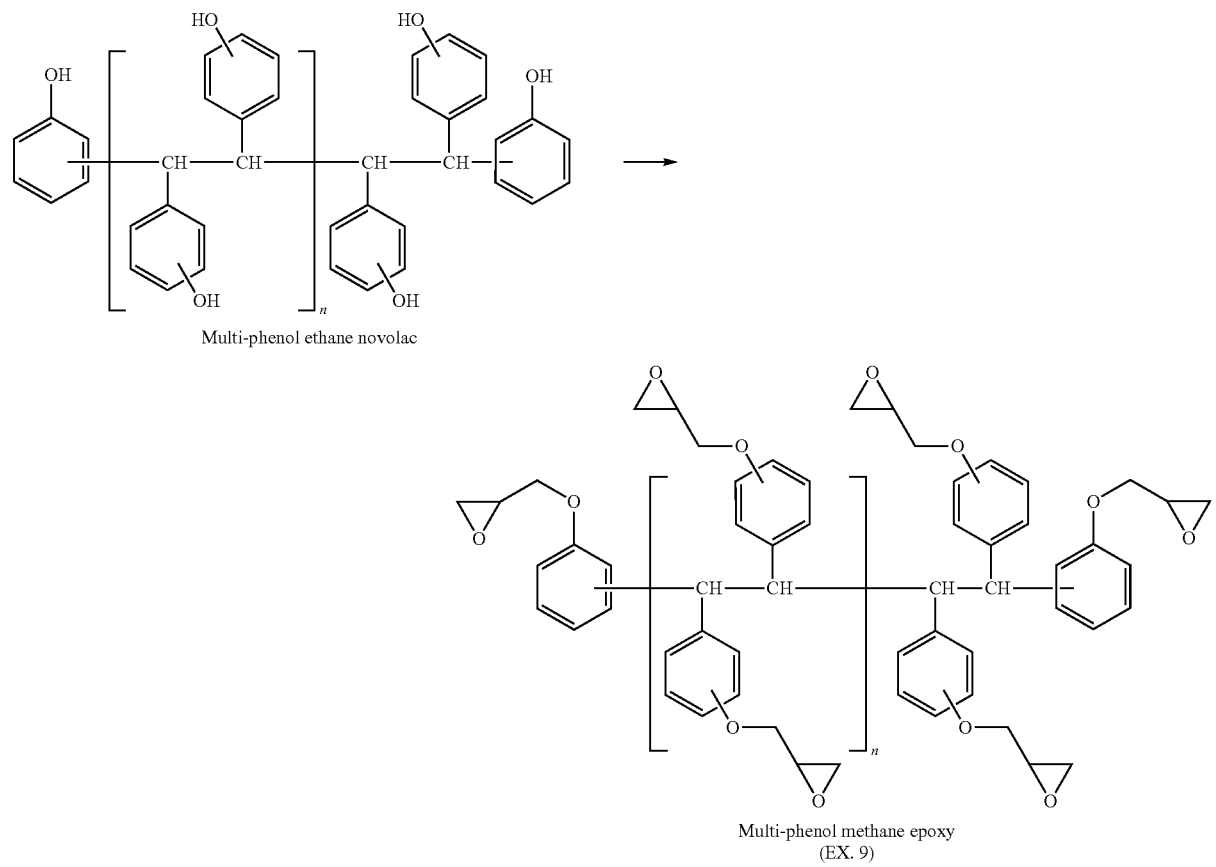

Multi-phenol ethane novolac

Multi-phenol methane epoxy
(EX. 9)

The above structure is a theoretical representation and, as noted above, numerous compounds having varying structures similar to the theoretical representation presented above are produced during the actual methods for forming products of glycidyl ethers of Example 9.

Example 10

Glycidyl ether of PF9110 was synthesized in accordance with the procedure described in Example 1, except that: PF9110 was used instead of the BPA of Example 1; the amount of epichlorohydrin was 1,550 g; the ratio of the ECH to the OH groups from PF9110 was 10.75 ([ECH]/[OH] =10.75); the content of glycidol and water in epichlorohydrin was 0.12 wt. % and less than 0.01 wt. % respectively; and the amount of 49.5 wt. % aqueous sodium hydroxide solution was 220 g.

An exemplary structure of a theoretical glycidyl ether of Example 10 and PF9110 is provided below to illustrate the core repeat unit of a theoretical glycidyl ether of Example 10.

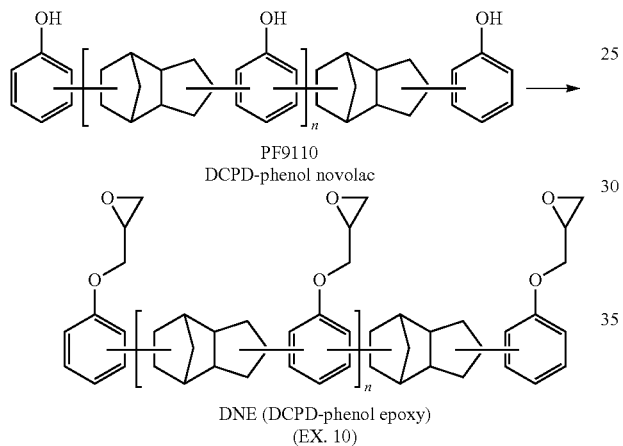

PF9110
DCPD-phenol novolac

DNE (DCPD-phenol epoxy)
(EX. 10)

The above structure is a theoretical representation and, as noted above, numerous compounds having varying structures similar to the theoretical representation presented above are produced during the actual methods for forming products of glycidyl ethers of Example 10.

Comparative Examples 8-10

Comparative Examples 8-10 are TFE1250, TNE190, and DNE260, respectively, which were commercial products obtained from Chang Chun Plastic.

Example 8 and Comparative Example 8 produced a product of glycidyl ethers having a core repeat unit that was multi-phenol methane. Example 9 and Comparative Example 9 produced a glycidyl ether having a repeat unit that was multi-phenol ethane. Example 10 and Comparative Example 10 produced a glycidyl ether having a repeat unit that was DCPD-phenol novolac. As shown in the Table 3, Examples 8-10 had lower α-glycol, lower OH value, and lower ICI viscosity properties. The EEW×HV value of Comparative Examples 8-10 were larger than 10, while the EEW×HV value of Examples 8-10 were less than 10.

Examples 11-16 and Comparative Examples 11-15

Resins were formed from the BPA glycidyl ethers of Examples 1-3 and Comparative Examples 1-3 as well as from the BPF glycidyl ethers of Examples 6 and 7 and Comparative Examples 5 and 6.

Specifically, glycidyl ethers of BPA of Examples 1-3 and Comparative Examples 1-3 as well as the glycidyl ethers of BPF of Examples 5 and 6 and Comparative Examples 5 and 6 were mixed with Isophorone diamine (hereafter "IPDA"), namely Baxxodur® EC 201 from BASF. The amine hydrogen equivalent weight (hereafter "AHEW") of IPDA is 43. The mass ratios of glycidyl ethers to IPDA are based on the equal mole (equivalent) of epoxy and amine hydrogen. For instance, using the resin formed from the BPA glycidyl ethers of Example 1, which had an EEW of 180.5 and an AHEW for IPDA of 43, the mass ratio and/or mass fraction of the BPA glycidyl ethers of Example 1 to IPDA may be determined as shown below:

$$\frac{(mass\_of\_glycidyl\_ether)/EEW}{(mass\_of\_hardener)/AHEW} = 1$$

$$\frac{5/180.5}{x/43} = 1 \Rightarrow x = 1.19(g)$$

The viscosity pot life was determined over a duration of time as the viscosity increased, e.g., up to 1,500 cps, for a mixture of resin and hardener by conducting a peak hold mode test using a TA Instruments Discovery Hybrid Rheometer HR-2 with 25 mm ETC Aluminum parallel plates. The glycidyl ethers were held at a temperature of 30° C.±0.5° C. with a nominal shear frequency of 100 1/s, nominal controlled strain amplitude of 5% and a gap of 1000 μm. The resin of glycidyl ethers was isothermally held until it hardened. The samples for glass transition temperature (hereafter "Tg") were cured at 80° C. for 12 h. Results of Tg of neat curing resins were carried out with a TA Q200 device in accordance with the methods of ASTM E1356.

Table 4 shows the properties of the resins formed from the BPA glycidyl ethers of Examples 11-13 and Comparative

TABLE 3

|  | EX.8 | EX.9 | EX.10 | CP.8 | CP.9 | CP.10 |
|---|---|---|---|---|---|---|
| [ECH]/[OH] | 6.53 | 6.67 | 10.75 | — | — | — |
| Catalyst (ppm) | 4,500 | 4,500 | 4,500 | — | — | — |
| EEW (g/eq) | 160.4 | 189.6 | 257.2 | 167.4 | 205.3 | 266.7 |
| HyCl (ppm) | 132 | 198 | 205 | 650 | 444 | 370 |
| ICl (60 Hz) | 0.53 | 4.68 | 1.92 | 0.74 | 6.66 | 2.78 |
| α-glycol (meq/g) | 0.0013 | 0.0019 | 0.0038 | 0.0964 | 0.0926 | 0.0677 |
| HV value (eq/100g) | 0.056 | 0.044 | 0.031 | 0.081 | 0.078 | 0.055 |
| EEW × HV (eq/eq) | 8.98 | 8.34 | 7.97 | 13.56 | 16.01 | 14.67 |

Figure 2:
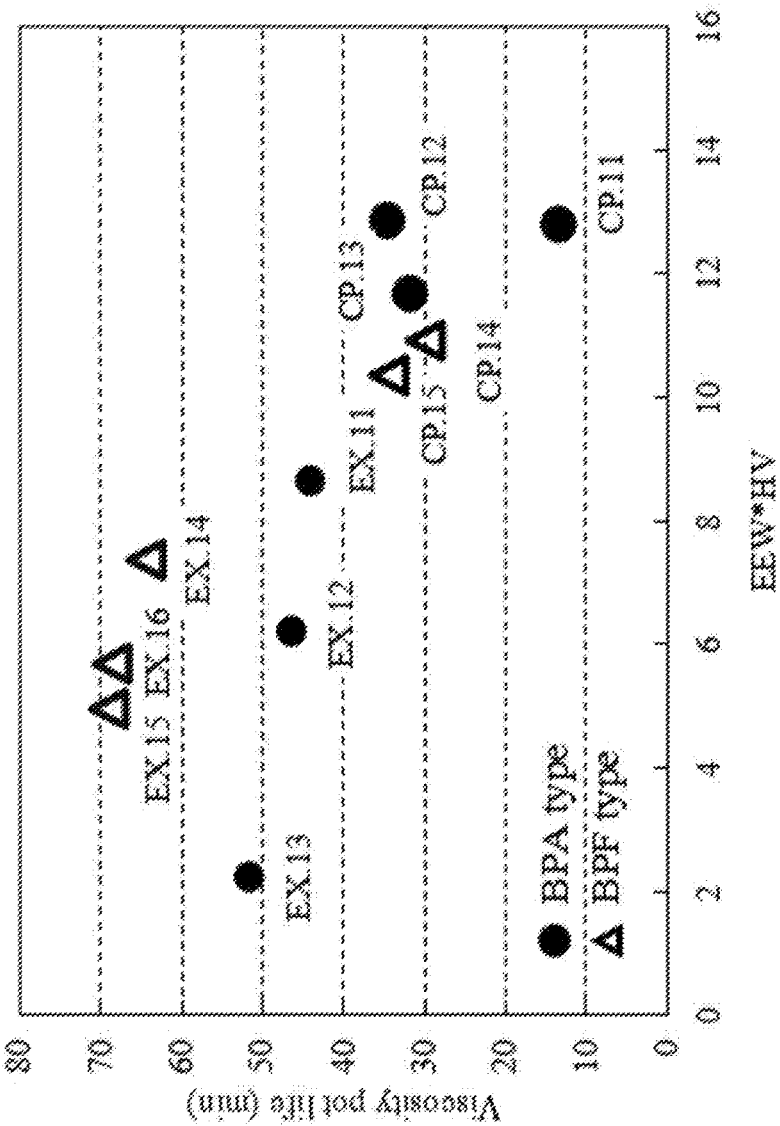
FIG. 2 is a scatter plot graph illustrating the effect of the EEW×HV value on the viscosity pot life for exemplary epoxy resins and comparative epoxy resins in accordance with aspects of the disclosure.

Examples 11-13. Table 5 shows the properties of the resins formed from the BPF glycidyl ethers of Examples 14-16 and Comparative Examples 14 and 15. As seen in FIGS. 1 and 2, an increase in the value of EEW×HV correlates to an increase in the viscosity pot life and glass transition temperature. Surprisingly, although the glycidyl ethers of Example 1 and Comparative Example 3 have similar values for EEW, the glycidyl ethers of this invention have higher Tg and longer viscosity pot life than that of comparative examples after curing.

TABLE 4

|  | EX.11 | EX.12 | EX.13 | CP.11 | CP.12 | CP.13 |
|---|---|---|---|---|---|---|
| Glycidyl ethers | EX.1 | EX.2 | EX.3 | CP.1 | CP.2 | CP.3 |
| EEW × HV (eq/eq) | 8.66 | 6.23 | 2.25 | 12.81 | 12.87 | 11.69 |
| Glycidyl ethers (g) | 5.00 | 5.00 | 5.00 | 5.00 | 5.00 | 5.00 |
| IPDA (g) | 1.19 | 1.21 | 1.24 | 1.16 | 1.19 | 1.20 |
| Vis. pot life (min) | 44.0 | 46.3 | 51.5 | 13.3 | 34.5 | 31.7 |
| Tg (° C.) | 152.7 | 154.3 | 156.1 | 129.2 | 135.0 | 137.1 |

TABLE 5

|  | EX.14 | EX.15 | EX.16 | CP.14 | CP.15 |
|---|---|---|---|---|---|
| Glycidyl ethers | EX.5 | EX.6 | EX.7 | CP.5 | CP.6 |
| EEW × HV (eq/eq) | 7.38 | 4.97 | 5.70 | 10.93 | 10.37 |
| Glycidyl ethers (g) | 5.00 | 5.00 | 5.00 | 5.00 | 5.00 |
| IPDA (g) | 1.31 | 1.34 | 1.36 | 1.26 | 1.29 |
| Vis. pot life (min) | 64.3 | 68.9 | 68.5 | 35.2 | 34.3 |
| Tg (° C.) | 137.4 | 140.1 | 138.9 | 129.8 | 136.4 |

The inventors discovered that typically for the same type of product of glycidyl ethers, the lower EEW of the glycidyl ether, the higher Tg of its cured resin. Additionally, it is believed that for products of glycidyl ethers having similar amounts of EEW, the contents of "HPLC n=0" and "MGE structure" contribute to increased Tg (see, e.g., the product of glycidyl ethers Example 1 and Comparative Example 3). While not being limited to any particular theory, the inventor believe that the amount of alpha glycol groups and OH groups in the glycidyl ether (HV value) will enhance curing rate. As a result, the lower content of alpha glycol and OH value, the longer viscosity pot life.

Additionally, the amount of isomer and oligomer content may reduce the viscosity and Tg. As shown in the Table 5, the differences of Tg for BPF glycidyl ethers between the Examples and Comparative Examples are not as large as that in the Table 4. It is believed that the reason for the difference is that the n=0 dimer content of BPF glycidyl ethers (Table 2) is much less than that of BPA glycidyl ethers (Table 1). However, the low value of EEW×HV of Example 5-7 still enhances Tg and increases viscosity pot life.

Examples 17-18 and Comparative Examples 16-17

Resins were formed from the glycidyl ethers of Example 1, Example 5, Comparative Example 3, and Comparative Example 6 and an IPDA/D230 solution. The IPDA/D230 solution contained about 25 wt. % of IPDA (AHEW=43) and 75 wt. % of D230 (AHEW=61), both of which were purchased from BASF, and AHEW of the blending IPDA/D230 is 55.22. The mass ratios were based on the equivalent weight of epoxy of glycidyl ethers and amine hydrogen equivalent weight of IPDA/D230. The mixtures of IPDA/D230 solution and the glycidyl ethers of Example 1, Example 5, Comparative Example 3, and Comparative Example 6 were cured for 8 hrs at a temperature of 80° C., annealed for 16 hrs at a temperature of 50° C., subsequently conditioned for 24 hrs at standard atmosphere to form cured resins.

The resins formed from the glycidyl ether of BPA from Example 1 and the glycidyl ether of BPF of Example 5 exhibited similar EEW values and consequently the amount of hardener used in each type of glycidyl ether are close to avoid the effects of hardener masking the improvements of the exemplary epoxy resins. As shown in the Table 6, the coefficient of thermal expansion (hereafter the "CTE") and the water absorption of Examples 17 and 18 are lower than that of Comparative Examples 16 and 17.

TABLE 6

|  | EX.17 | CP.16 | EX.18 | CP.17 |
|---|---|---|---|---|
| Type of glycidyl ethers | BPA-type | | BPF-type | |
| Glycidyl ethers | EX.1 | CP.3 | EX.5 | CP.6 |
| EEW of glycidyl ethers | 180.5 | 179.8 | 163.9 | 167.2 |
| Glycidyl ethers (g) | 100.0 | 100.0 | 100.0 | 100.0 |
| D230/IPDA = 75/25 w/w(g) | 30.6 | 30.7 | 33.7 | 33.0 |
| CTE, α (50° C.-70° C., ppm/° C.) | 24 | 51 | 19 | 34 |
| Water absorption (100° C. 1 h, wt %) | 0.9 | 1.3 | 1.0 | 2.2 |

Examples 19-20 and Comparative Examples 18-19

Resins were formed from the glycidyl ethers of Example 1, Example 5, Comparative Example 3, and Comparative Example 6 and 1,4-Butanediol diglycidyl ether (hereafter "BDGE125") obtained from Chang Chun Plastic. The mass ratio was 85 wt. % of glycidyl ethers to 15 wt. % of BDGE125 (EEW=125.5). The IPDA/D230 employed as a hardener had a mass ratio of 25 to 75, and AHEW of the blending IPDA/D230 is 55.22.

The mass ratios of the hardener to the mixtures of BDGE125 and specific glycidyl ethers were based on the equivalent weight of epoxy of glycidyl ethers and amine hydrogen equivalent weight of the hardener. The resins were cured for 8 hrs at a temperature of 80° C., annealed for 16 hrs at a temperature of 50° C., subsequently conditioned for 24 hrs at standard atmosphere. The mechanical properties of the cured resins formed from Example 1, Example 5, Comparative Example 3, and Comparative Example 6 are provided in the Table 7, below.

TABLE 7

|  | EX.19 | CP.18 | EX.20 | CP.19 |
|---|---|---|---|---|
| Type of glycidyl ethers | BPA-type | | BPF-type | |
| Glycidyl ethers | EX.1 | CP.3 | EX.5 | CP.6 |
| EEW of blended glycidyl ethers | 169.4 | 168.8 | 156.7 | 159.3 |
| Blended glycidyl ethers (g) | 100.0 | 100.0 | 100.0 | 100.0 |
| IPDA/D230 (g) | 32.6 | 32.7 | 35.2 | 34.7 |
| Tensile Strength (Mpa) | 69 | 64 | 69 | 59 |
| Tensile Elongation (%) | 4.2 | 3.8 | 3.8 | 3.1 |
| Tensile Elongation at Break (%) | 7.6 | 6.0 | 5.0 | 4.3 |
| Tensile Modulus (Mpa) | 2,640 | 2,670 | 2,897 | 2,788 |
| Flexural Strength (Mpa) | 110 | 107 | 110 | 109 |
| Flexural Elongation (%) | 6.8 | 6.0 | 6.7 | 6.2 |
| Flexural Modulus (Mpa) | 3,080 | 2,870 | 3,120 | 3,435 |

Figure 3:
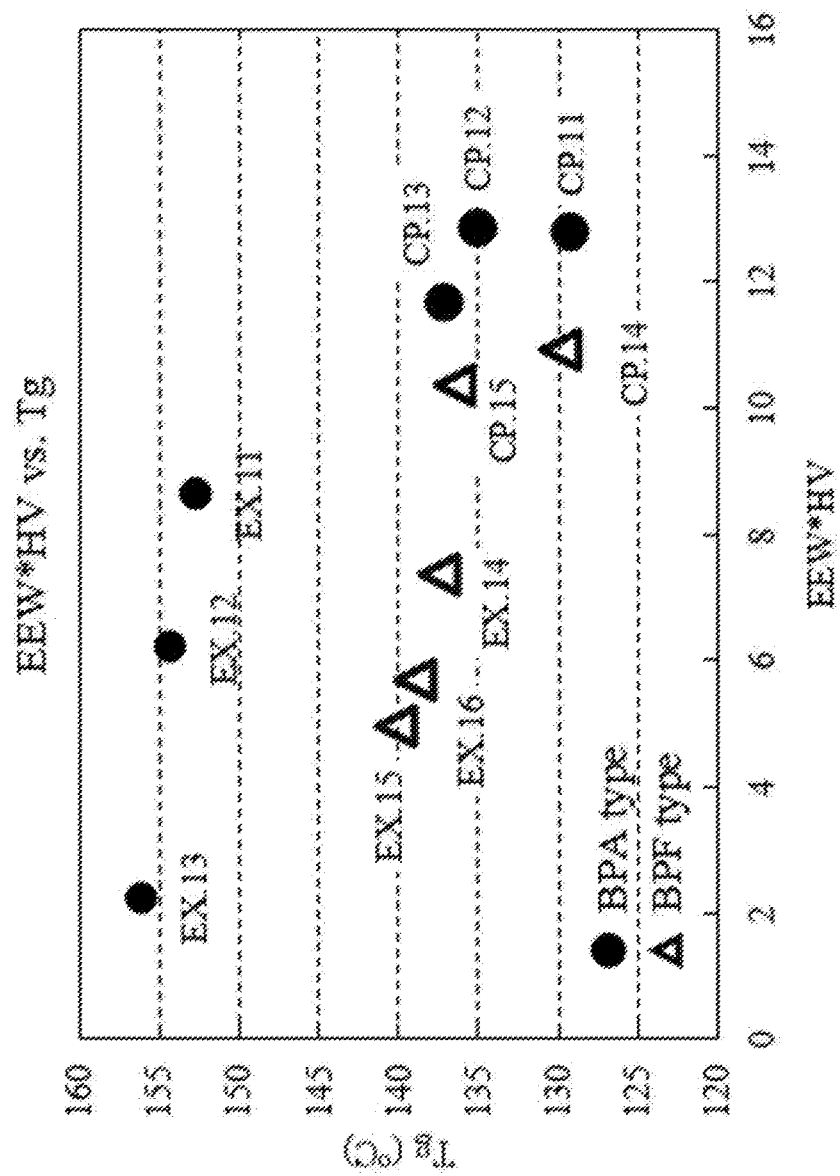
FIG. 3 is a scatter plot graph illustrating the effect of the EEW×HV value on the glass transition temperature (Tg) for exemplary epoxy resins and comparative epoxy resins in accordance with aspects of the disclosure.

The cured resins formed from Examples 1 and 5, not only exhibited higher strength and modulus in tensile and flexural testing, but also exhibited better elongation properties than the cured resins from Comparative Examples 3 and 6. FIG. 2 provides a scatter plot graph illustrating the effect of the EEW×HV value on the viscosity pot life for exemplary epoxy resins 11-16 and comparative epoxy resins 11-15. FIG. 3 provides a scatter plot graph illustrating the effect of the EEW×HV value on the glass transition temperature (Tg) for exemplary epoxy resins 11-16 and comparative epoxy resins 11-15.

As used herein, all ranges provided are meant to include every specific range within, and combination of sub ranges between, the given ranges. Additionally, all ranges provided herein are inclusive of the end points of such ranges, unless stated otherwise. Thus, a range from 1-5, includes specifically 1, 2, 3, 4 and 5, as well as sub ranges such as 2-5, 3-5, 2-3, 2-4, 1-4, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense. The terms "a," "an," and "the" are understood to encompass the plural as well as the singular. The expression "one or more" means "at least one" and thus may include an individual characteristic or mixtures/combinations.

Other than in the operating examples, or where otherwise indicated, all numbers expressing quantities of ingredients and/or reaction conditions may be modified in all instances by the term "about," meaning within +/−5% of the indicated number. The term "substantially free" or "essentially free" as used herein means that there is less than about 2% of the specific characteristic. All elements or characteristics positively set forth in this disclosure can be negatively excluded from the claims.

What is claimed is:

1. A product of glycidyl ether of a mono or polyhydric phenol comprising 48 to 300 ppm of hydrolyzable chlorine, an epoxy equivalent weight (EEW), and a hydroxyl value (HV), wherein the EEW unit is gram/equivalent (g/eq), the HV unit is equivalent/100 gram (eq/100 g), and EEW×HV=1 to 10 (eq/100 eq).

2. The product of glycidyl ether of a mono or polyhydric phenol of claim 1, wherein EEW×HV=1 to 9 (eq/100 eq).

3. The product of glycidyl ether of a mono or polyhydric phenol of claim 1, comprising 0.0001 to 0.11 mEq/g of alpha-glycol glyceryl ether groups.

4. The product of glycidyl ether of a mono or polyhydric phenol of claim 1, wherein the EEW is 150 to 200 g/eq.

5. The product of glycidyl ether of a mono or polyhydric phenol of claim 1, wherein the HV is from 0.01 to 0.06 eq/100 g.

6. The product of glycidyl ether of a mono or polyhydric phenol of claim 1, wherein the polyhydric phenol is selected from resorcinol, hydroquinone, 2,2-bis-(4'-hydroxyphenyl)-propane (bisphenol A), mixtures of isomers of dihydroxy-diphenyl methane (bisphenol F), 4,4'-di-hydroxydiphenyl cyclohexane, 4,4'-dihydroxy-3,3'-dimethyldiphenyl propane, 4,4'-dihydroxydiphenyl, 4,4'-dihydroxybenzophenone, bis-(4'-hydroxyphenyl)-1,1-ethane, bis-(4'-hydroxyphenyl)-1,1-isobutane, bis-(4'-hydroxy-tert.-butylphenyl)-2,2-propane, bis-(2-hydroxy-naphthyl)-methane, 1,5-dihydroxynaphthalene, tris-(4-hydroxyphenyl)-methane, and bis-(4-hydroxy-phenyl) ether, bis-(4-hydroxyphenyl) sulfone, phenol novolak, brominated phenol novolak, o-cresol novolak, resorcin novolak, brominated resorcin novolak, tris(hydroxyphenyl)methane, tetraphenol ethane phenolic resin, aldehyde-polyphenolic condensates, dicyclopentadiene-phenolic resins, 9,10-dihydro-9-oxa-10-phosphaphenanthrene-10-oxide (DOPO) phenolic resins, and a combination thereof.

7. An epoxy resin composition comprising:
   i) the product of glycidyl ether of a mono or polyhydric phenol of claim 1; and
   ii) a hardener.

8. The epoxy resin composition of claim 7, wherein the hardener is selected from polyetheramine, Isophoronediamine, 4,4-Diaminodicyclohexylmethane, 4,4'-methylenebis(2-methylcyclohexyl-amine), 4-methyl-1,3'-cyclohexanediamine, Dicyandiamide, imidazoles, phenol novolak, diaminodiphenylmethane, diaminodiphenylsulfone, m-phenylenediamine, phthalic anhydride, tetrahydrophthalic anhydride, pyrromellitic anhydride, benzophenone tetracarboxylic anhydride, and a combination thereof.

9. The epoxy resin composition of claim 7, wherein the hardener is isophoronediamine and wherein the glass transition temperature of the epoxy resin composition is more than 137° C.

10. The epoxy resin composition of claim 7, wherein the hardener is isophoronediamine and wherein the viscosity pot life of the epoxy resin composition at a temperature of 30° C. is from 40 to 100 minutes.

11. A process for producing the product of glycidyl ether of a mono or polyhydric phenol of claim 1 comprising:
   (a) reacting an epihalohydrin with a mono or polyhydric phenol in the presence of a catalyst to produce a halohydrin ether; and
   (b) dehalogenating the halohydrin ether to form the product of glycidyl ether of a mono or polyhydric phenol.

12. The process of claim 11, wherein the reaction of the epihalohydrin with a mono or polyhydric phenol is carried out at a temperature of 30° C. to 80° C.

13. The process of claim 11, wherein a molar ratio of the epihalohydrin to hydroxyl groups of the mono or polyhydric phenol is from 3.5:1 to 11.0:1.

14. The process of claim 11, wherein not more than 2 wt. % glycidol, based on the total weight of the epihalohydrin, is present during the reaction of the epihalohydrin with the mono or polyhydric phenol.

15. The process of claim 11, wherein not more than 1 wt. % of water, based on the total weight of the epihalohydrin, is present during the reaction of the epihalohydrin with the mono or polyhydric phenol.

16. The process of claim 11, wherein the halohydrin is dehalogenated using a base, the base is selected from NaOH, KOH, $Na_2CO_3$, $K_2CO_3$, and a combination thereof.

17. The process of claim 11, wherein the catalyst is an onium salt in an amount of 1,000 to 9,000 ppm, relative to the total amount of mono or polyhydric phenol, the onium salt is selected from benzyltributylammonium chloride, benzyltriethylammonium chloride, benzyltrimethylammonium chloride, tetrabutylammonium bromide, tetramethylammonium chloride, tetrabutylammonium hydrogen sulfite, trioctylmethylammonium chloride, and a combination thereof.

18. A process for producing the product of glycidyl ether of a mono or polyhydric phenol of claim 1 comprising:
   (a) reacting an epihalohydrin with a mono or polyhydric phenol at a temperature of 30° C. to 80° C. in the presence of an onium salt to produce a halohydrin ether, wherein:

a molar ratio of the epihalodyrin to hydroxyl groups of the mono or polyhydric phenol is from 3.5:1 to 11.0:1;

the onium salt is present in an amount of 1,000 to 9,000 ppm, relative to the total amount of mono or polyhydric phenol;

not more than 2 wt. % of glycidol is present, based on the total weight of the epihalohydrin; and not more than 1 wt. % water is present, based on the total weight of the epihalohydrin; and (b) dehalogenating the halohydrin ether with a base to form the glycidyl ether of a mono or polyhydric phenol product.

19. The process of claim 18, wherein the onium salt is selected from benzyltributylammonium chloride, benzyltriethylammonium chloride, benzyltrimethylammonium chloride, tetrabutylammonium bromide, tetramethylammonium chloride, tetrabutylammonium hydrogen sulfite, trioctylmethylammonium chloride, and a combination thereof.

* * * * *